United States Patent [19]

Grandon

[11] Patent Number: 4,578,058
[45] Date of Patent: Mar. 25, 1986

[54] INTRAOCULAR CATHETER APPARATUS AND METHOD OF USE

[76] Inventor: Stanley C. Grandon, 4529 Tanbark, Bloomfield Hills, Mich. 48013

[21] Appl. No.: 595,676

[22] Filed: Apr. 2, 1984

[51] Int. Cl.⁴ .............................................. A61M 1/00
[52] U.S. Cl. ....................................... 604/27; 604/28; 604/93; 604/43; 623/4
[58] Field of Search ...................... 604/27, 28, 43–45, 604/93, 94, 264, 281, 284; 3/13

[56] References Cited

U.S. PATENT DOCUMENTS

| | | | |
|---|---|---|---|
| 3,065,749 | 11/1962 | Brass | 604/35 |
| 4,117,836 | 10/1978 | Erikson | 604/281 |
| 4,300,550 | 11/1981 | Gandi et al. | 604/35 |
| 4,405,313 | 9/1983 | Sisley et al. | 604/43 |
| 4,468,216 | 8/1984 | Muto | 604/43 |

Primary Examiner—J. L. Kruter
Attorney, Agent, or Firm—Krass and Young

[57] ABSTRACT

Surgical catheter apparatus for catheterized intraocular irrigation and aspiration, and a method of use are provided. The apparatus has an elongated body comprising an aspiration tube and an irrigation tube in double-barrel relation for transport of fluid, each tube having proximal and distal portions in which the distal portion is curved in a compound curve comprising both lateral curvature and transverse curvature. The distal portion includes an aspiration port and an irrigation port, the aspiration port being end-located and spaced on the curvature away from the irrigation port.

10 Claims, 9 Drawing Figures

INTRAOCULAR CATHETER APPARATUS AND METHOD OF USE

DESCRIPTION

1. Technical Field

This invention relates to surgical apparatus and its use, and, more particularly, to a unique kind of catheter apparatus for catheterized intraocular irrigation and aspiration.

2. Background of the Invention

In the human eye, the lens is situated behind the pupil and iris, and functions to focus light entrant through the cornea and pupil onto the retina at the rear of the eye. The lens is a biconvex, highly transparent structure surrounded by a thin capsule. The lens capsule is supported at its periphery by suspensory ligaments, called zonules, that are continuous with the ciliary muscle. Contraction of this muscle relaxes the zonules, allowing the lens to become more spherical, thereby altering its focal length.

A cataract condition results when the material within the lens capsule becomes clouded, thereby obstructing the passage of light.

To correct this condition, two forms of surgery are used. In intracapsular cataract extraction, the entire lens is removed intact. To accomplish this, the surgeon severs the zonules or suspensory ligaments about the entire periphery of the capsule, and removes the entire lens with the capsule and its content material intact.

In extracapsular cataract extraction, an incision is made through the front wall (the "anterior capsule") of the lens, and the clouded cellular material within the capsule is removed through this opening, including the lining or cortex of the capsule. Various scraping, suction or phacoemulsification techniques are used to accomplish such extraction. The transparent rear capsule wall (the "posterior capsule") remains in place in the eye. Also remaining in place are the zonules and peripheral portions of the anterior capsule.

After capsulotomy and removal of any formed nucleus, the incision is closed with temporary sutures and the anterior chamber is filled with balanced salt solution. A 23-gauge blunt cannula with a side aperture near the tip is attached to suitable instrumentation such as a fluid-filled syringe with a Luer-Lok adapter. The cannula tip is introduced into the cortex in the capsular cleft or fornix, and a slight suction is drawn that causes the cortex to occlude the cannula's aperture, creating a microerysiphake effect. This makes it possible to strip cortex from the capsular fornix without aspirating it through the cannula. Slight positive pressure of the syringe negates the suction and releases the cortex from the microerysiphake.

The procedure is repeated in all quadrants until all cortex is dislodged.

Certain precautions are taken to avoid inadvertent posterior capsule or zonule rupture during cortex aspiration. When the cannula is in the capsular fornix only enough suction is used to grasp the cortex and strip and move it centrally, where greater depth of the capsular bag and chamber facilitates aspiration. Unless the pupil remains well dilated throughout the procedure the cortex is hidden behind the iris, making aspiration a blind procedure. The usual practice is to slowly and gently strip the cortex (without aspiration) from the fornix and pull it centrally to where the capsular bag and chamber are deepest and aspiration is done under direct visualization.

When cortex occludes the aspiration port, pressure builds up. When the cortex suddenly passes into the cannula, a surge of suction pressure may momentarily shallow the chamber enough to cause posterior capsule engagement by the aspiration port. If the cannula is moving at all when this inadvertent capsule engagement occurs, the capsule will tear. Conversely, even if the capsule is forcefully grasped but no cannular movement occurs, it will not tear. Complete and gentle removal of the nucleus and cortex is essential since capsule rupture and incomplete removal of lens material and lens cortex may prevent safe implantation.

OBJECTS OF THE INVENTION

It is therefore an object of the present invention to provide an improved apparatus and surgical method for removal of cortical tissue.

Another object of the invention is to provide an improved extractor apparatus and a method for irrigating the intraocular capsule and aspirating the same for safe and complete removal of cortex from the capsule.

These and other objects, features and advantages of the invention will be seen from the following detailed description and the accompanying drawings.

DETAILED DESCRIPTION OF THE INVENTION

The present invention in one aspect concerns surgical catheter apparatus for catheterized intraocular irrigation and aspiration of tissue, especially cortical tissue, from within the eye. The catheter, in a preferred embodiment has an axially elongated tubular body comprising an aspiration tube and an irrigation tube in double-barrel relation for transport of fluid into and from the eye. Each tube has a proximal portion and a distal portion. In one preferred embodiment, the distal portion is curved with respect to the axial line of the proximal portion, in a compound curve comprising both lateral curvature and transverse (that is, either anterior or posterior) curvature. The compound curvature comprises lateral curvature to the right or to the left as desired so that the distal portion can be directed to a particular quadrant to the right or the left. The magnitude of curvature is such that when inserted in the lensless (aphakic) eye capsule the terminal end or extremity of the distal portion of the aspiration tube is engageable or contactable for extraction purposes, with capsular cortex, particularly cortical tissue that is behind the iris or otherwise located in remote or normally inaccessible portions such as equitorial cortex, cortex in the fornices, and peripheral cortex in the upper lateral and posterior regions of the capsule. The distal portion of the catheter includes an aspiration port and an irrigation port. The aspiration port is located at the extremity or outer end of the distal portion, and, relative to the irrigation port, is spaced on the curvature away from the latter port. As indicated, the aspiration and irrigation tubes of the tubular body are in double-barrel relation, preferably side-by-side or over-and-under, preferably with the aspiration port located on the top side, and preferably immediately adjacent to the outer end of the distal portion. The irrigation port is located preferably on the side of the distal portion positioned so that irrigation discharge is directed centrally within the eye chamber and away from the zone of aspiration, preferably on a tangent to the curvature.

In one preferred embodiment, the compound curvature is gradual and approximates 180° lateral curvature and 15° posterior curvature, dimensioned and with geometry such that the distal end, when inserted through an incision in the top of the eye, can be directed under the iris then into the capsule and in turn to an uppermost equitorial site or 12 o'clock position without adversely displacing or disturbing the configuration or integrity of the capsule. In another preferred embodiment, the compound curvature is gradual and approximates 90° lateral curvature and 15° anterior curvature, dimensioned so that the distal end, when inserted through an incision in the top of the eye, can be directed under the iris, then into the capsule and in turn to a lateral equitorial site without adversely displacing or disturbing the configuration or integrity of the capsule.

The present invention in another aspect concerns a surgical procedure for dislodging tissue such as cortical tissue from the eye capsule, comprising the steps of inserting below the iris a catheter having a curved distal portion, according to the invention as described, that is engageable as inserted with cortical tissue of a given quadrant of the capsule, and stripping and aspirating the tissue from the eye. In a preferred embodiment, the method employs a separate, curved catheter for each quadrant, namely right and left curved catheters for the respective right and left upper quadrants and right and left curved catheters for the respective right and left lower quadrants.

DESCRIPTION OF THE DRAWINGS

The invention will be more fully understood by reference to the following detailed description and accompanying drawings in which:

FIG. 2 is a side view of the catheter shown in FIG. 1a;

FIG. 4 is a side view of the catheter shown in FIG. 3a;

Referring to the drawings, FIGS. 1a, 1b, and 2 show a preferred catheter 10 of the invention for irrigating and aspirating lens material from lateral left and right zones or areas of the lens capsule. The catheter 10 includes a tubular body 11 comprising an aspiration tube 12 and an irrigation tube 13. Each tube has a proximal portion 14 and a distal portion 15. The distal portion is curved in a compound right angle curve comprising both lateral curvature 16a (as shown in FIGS. 1a and 1b) and anterior curvature 16b (as shown in FIG. 2). The distal portion 15 includes an aspiration port 17 located on the top 12a and at the end 12b of the aspiration tube; it also includes an irrigation port 18 located on the side 13a and end 13b of the irrigation tube 13 and, at a tangent to the lateral curvature of the compound curve 16.

FIGS. 3a, 3b and 4 show a preferred catheter 20 of the invention for irrigating and aspirating lens material from upper or superior left and right zones of the lens capsule. The catheter 20 includes a tubular body 21 comprising an aspiration tube 22 and an irrigation tube 23. Each tube has a proximal portion 24 and a distal portion 25. The distal portion is curved in a compound reverse curve comprising lateral curvature 26a (as shown in FIGS. 3a and 3b) and posterior curvature 26b (as shown in FIG. 4). The distal portion 25 includes an aspiration port 27 located in the top 22a and at the end 22b of the aspiration tube; it also includes an irrigation port 28 located on the side 23a and end 23b of the irrigation tube and at a tangent to the lateral curvature of the compound curve.

Figure 1A:
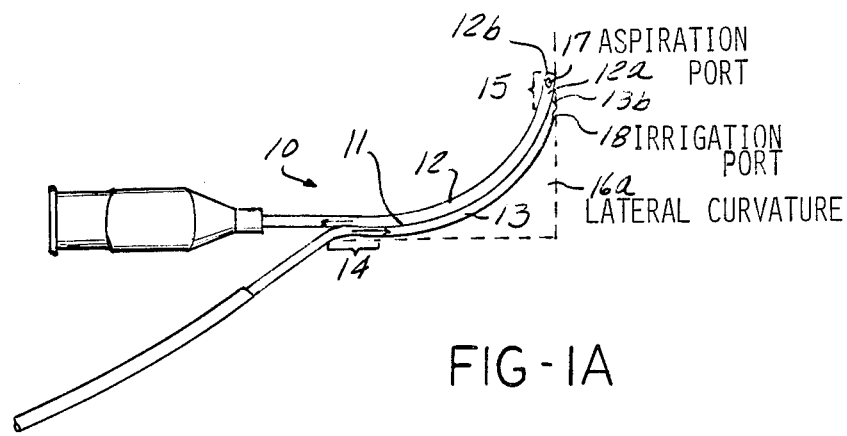
FIGS. 1a and 1b are top views of left and right embodiments respectively of a preferred embodiment of an irrigating aspirating catheter according to the invention.
Figure 1B:
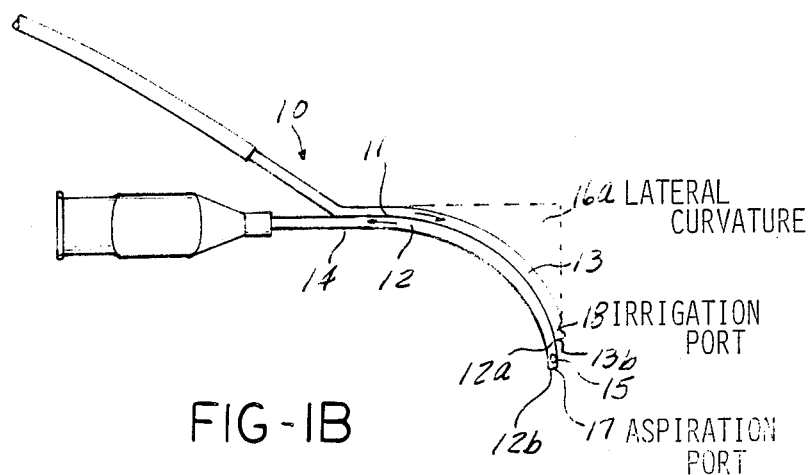
Figure 2:
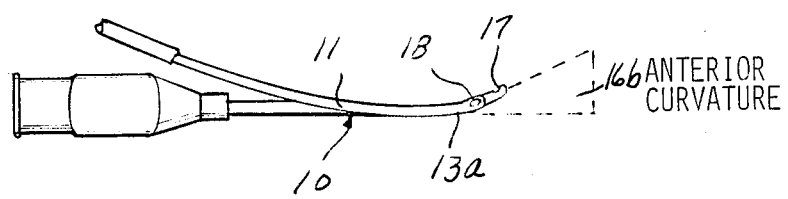
Figure 3A:
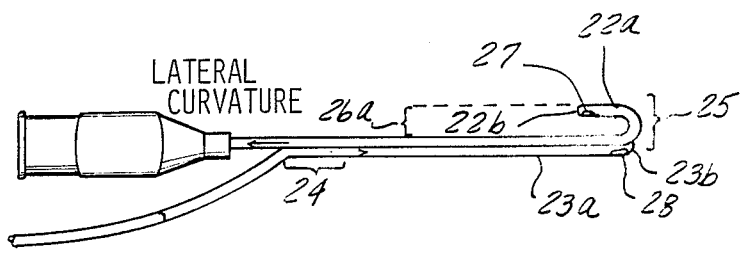
FIGS. 3a and 3b are top views of left and right oriented embodiments respectively of another preferred embodiment of an irrigating aspirating catheter according to the invention.
Figure 3B:
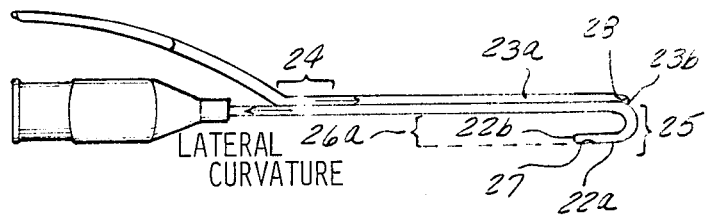
Figure 4:
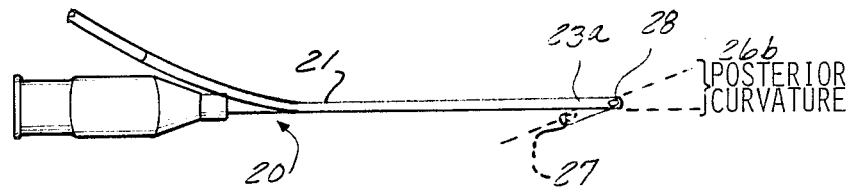
Figure 5:
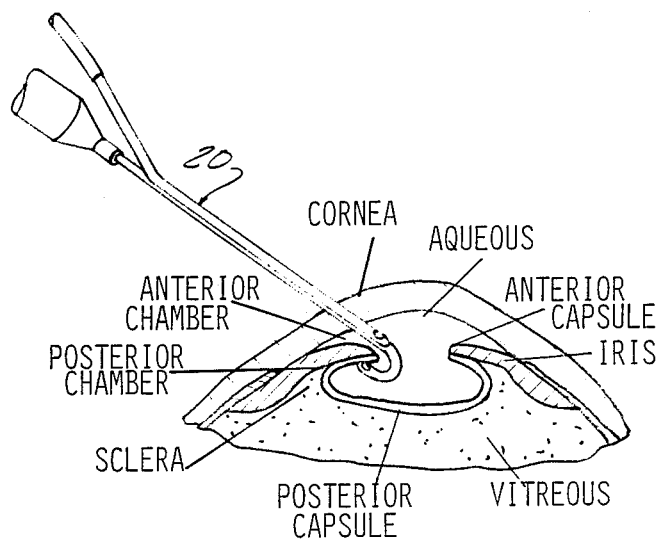
FIG. 5 is a schematic view of the catheterized human eye, partly in vertical section, according to the invention.
Figure 6:
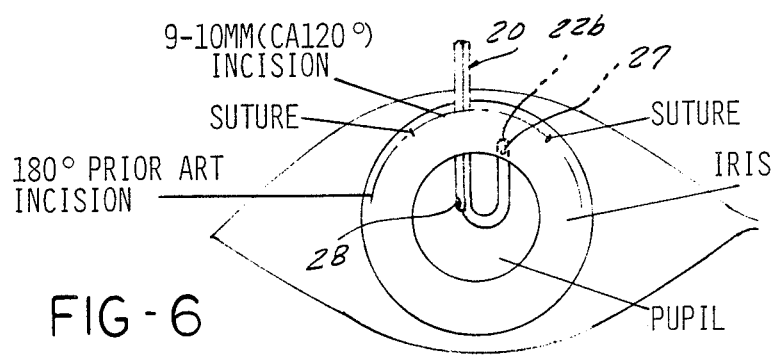
FIGS. 6 and 7 are frontal plan views of the catheterized eye according to the invention.
Figure 7:
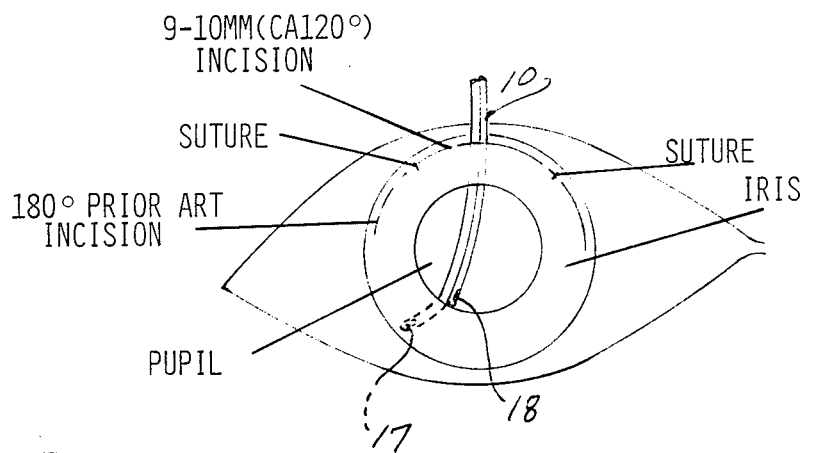

For extraction of the upper portion of the capsular chamber, according to one preferred procedure, the reverse-curved catheter 20 is inserted by the surgeon into the closed chamber through a sutured incision (as shown in FIGS. 5 and 6). In the prior art procedures an incision of about 180° was required to enable the required sidewise insertion of conventional catheters for stripping. In contrast and as a significant advantage, the preferred procedure of the present invention uses only a segment of the incision and the incision in turn is only about 120°. The catheter is inserted so that the distal portion 25 passes under the opening of the iris, in turn, so that and the end 22b of the aspiration tube is engaged with the cortex (not shown) behind the iris. In this way, and by moving the aspiration port 27 successively to all of the upper areas of the capsular chamber, both quadrants in the entire upper portion of the chamber can be irrigated and stripped of cortex and in due course aspirated, in the general manner described above, using in succession the left and right oriented catheters shown in FIGS. 3a and 3b. The posterior curvature of the catheters is particularly effective for extraction of these areas. Similarly, the right-angle curved catheters 10 may be used (as shown in FIG. 7) for extracting material from the middle and lower left and right portions of the quadrants. The anterior curvature of the catheters is particularly effective for extraction of these areas.

For control of the fluid pressure in the chamber, the irrigation tube is supplied with fluid in conventional fashion, for example, through suitable tubing preferably silicone tubing (of suitable length, e.g., 80 mm. in length) connected by Luer-Lok means with a gravity-fed supply of irrigation fluid. Aspiration may be supplied in any suitable way, preferably from a syringe by Luer-Lok attachment of the aspiration tube with a syringe. The cannula, including the irrigation and aspiration tubes can be made using conventional materials and methods, preferably of surgical quality stainless steel, the tubing in one preferred embodiment being, for example, 23-gauge tubing. In a preferred form, the spacing between the aspiration port and the irrigation port is about 3 mm. For the reverse curve cannula, the lateral curvature is about 180°, the transverse curvature about 15°, and the axial length of the cannula about 27 mm. For the right-angle curve cannula, the lateral curvature is about 90°, the transverse curvature about 15°, and the axial length about 27 mm.

What is desired to claim as my exclusive property in the invention, as described, is the following.

We claim:

1. Surgical catheter apparatus for catheterized intraocular irrigation and aspiration of an aphakic eye, having an axially elongated tubular body along a longitudinal axis comprising an aspiration tube and an irrigation tube in double-barrel side by side relation for transport of fluid therein, each tube having a proximal portion and a distal portion, said distal portion with respect to the longitudinal axis of the proximal portion having a permanently fixed curved portion forming a compound curve means comprising both lateral curvature means and transverse curvature means with respect to the longitudinal axis, the degree of curvature means being such that during aspiration the curved extremity of the distal portion of the aspiration tube engages the capsular cortex behind the iris in the posterior chamber in the capsule of a aphakic eye, said distal portion including an aspiration port and an irrigation port, the aspiration port being located at the extreme distal portion and being spaced apart on the curvature in a direction facing away from the irrigation port on the distal end of the aspiration tube.

2. A surgical catheter according to claim 1 where the distal portion of the catheter is laterally curved in a compound curve to the right when the longitudinal axis of said proximal portion extends horizontally when viewed by an on looker.

3. A surgical catheter according to claim 1 where the distal portion of the catheter is laterally curved in a compound curve to the left when the longitudinal axis of said proximal portion extends horizontally when viewed by an on looker.

4. A surgical catheter according to claims 2 or 3 where the angle of curvature is about 90° lateral.

5. A surgical catheter according to claims 2 or 3 where the angle of curvature is about 180° lateral.

6. A surgical catheter according to claim 1 where the curvature is about 15° transverse to a plane formed by said proximal end and the lateral curvature means.

7. A surgical catheter according to claim 1 wherein the aspiration port faces an onlooker in a plane generated by the longitudinal axis of said proximal and distal end of the catheter.

8. A surgical catheter according to claim 7 where the irrigation port is located in a plane 90° to said horizontal plane at the distal end of the irrigation tube.

9. A surgical procedure for dislodging tissue from the eye capsule, comprising the steps of inserting below the iris a curved distal portion means of the catheter according to claim 1, and stripping and aspirating the tissue from the eye.

10. A surgical procedure according to claim 9, comprising dislodging tissue successively from each of the four quadrants of the eye capsule employing a separate curved catheter for each quadrant, the catheters being right and left curved catheters for the respective right and left upper quadrants and right and left catheters for the respective right and left lower quadrants.

* * * * *